US011089751B2

(12) United States Patent
Lemont

(10) Patent No.: US 11,089,751 B2
(45) Date of Patent: Aug. 17, 2021

(54) LETTUCE VARIETIES 'EZTHANA' AND 'EZTRON'

(71) Applicant: Enza Zaden Beheer B.V., Enkhuizen (NL)

(72) Inventor: Magali Lemont, Longue (FR)

(73) Assignee: Enza Zaden Beheer B.V., Enkhuizen (NL)

( * ) Notice: Subject to any disclaimer, the term of this patent is extended or adjusted under 35 U.S.C. 154(b) by 532 days.

(21) Appl. No.: 15/979,155

(22) Filed: May 14, 2018

(65) Prior Publication Data

US 2018/0332813 A1 Nov. 22, 2018

Related U.S. Application Data

(60) Provisional application No. 62/508,208, filed on May 18, 2017.

(51) Int. Cl.
*A01H 6/14* (2018.01)
*A01H 5/12* (2018.01)
*A01H 1/04* (2006.01)
*A01H 4/00* (2006.01)
*A01H 1/06* (2006.01)

(52) U.S. Cl.
CPC ............ *A01H 6/1472* (2018.05); *A01H 1/04* (2013.01); *A01H 5/12* (2013.01); *A01H 1/06* (2013.01); *A01H 4/008* (2013.01)

(58) Field of Classification Search
None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,777,196 A | 7/1998 | Hall | |
| 5,850,009 A | 12/1998 | Kevern | |
| 5,948,957 A | 9/1999 | Chapko et al. | |
| 5,959,185 A | 9/1999 | Streit et al. | |
| 5,969,212 A | 10/1999 | Getschman | |
| 5,973,232 A | 10/1999 | Waycott et al. | |
| 5,973,234 A | 10/1999 | Mueller et al. | |
| 5,977,445 A | 11/1999 | Soper et al. | |
| 6,492,579 B2 | 12/2002 | Olivas et al. | |
| 6,903,249 B2 | 6/2005 | Lambalk et al. | |
| 7,115,799 B2 | 10/2006 | De Jong | |
| 7,371,934 B1 | 5/2008 | Skrsyniarz | |
| 7,427,699 B1 | 9/2008 | Skrsyniarz | |
| 7,501,555 B2 | 3/2009 | Lambalk et al. | |
| 7,534,941 B1 | 5/2009 | Avila et al. | |
| 7,579,520 B1 | 8/2009 | Knerr | |
| 7,705,206 B2 | 4/2010 | Waycott | |
| 7,790,948 B2 | 9/2010 | Lambalk et al. | |
| 7,960,617 B2 | 6/2011 | Knerr | |
| 7,977,536 B2 | 7/2011 | Holland et al. | |
| 8,183,437 B2 | 5/2012 | Waycott | |
| 8,188,340 B2 | 5/2012 | Holland et al. | |
| 8,193,416 B1 | 6/2012 | Peng | |
| 8,203,034 B2 | 6/2012 | Waycott | |
| 8,212,114 B2 | 7/2012 | Holland et al. | |
| 8,212,115 B2 | 7/2012 | Holland et al. | |
| 8,212,116 B2 | 7/2012 | Lemont et al. | |
| 8,373,026 B2 | 2/2013 | Pallottini | |
| 8,389,810 B2* | 3/2013 | Ammerlaan | A01H 5/00 435/410 |
| 8,404,935 B2 | 3/2013 | Holland | |
| 8,404,936 B2 | 3/2013 | Skrsyniarz | |
| 8,410,338 B2 | 4/2013 | Conijn | |
| 8,450,563 B2 | 5/2013 | Nannes | |
| 8,471,105 B2 | 6/2013 | Holland | |
| 8,471,106 B2 | 6/2013 | Lemont | |
| 8,476,494 B2 | 7/2013 | Nannes | |
| 8,476,495 B2 | 7/2013 | Skrsyniarz | |
| 8,476,499 B2 | 7/2013 | Nannes | |
| 8,558,063 B2 | 10/2013 | Lemont | |
| 8,592,654 B2 | 11/2013 | Conijn et al. | |
| 8,692,074 B2 | 4/2014 | Sinclair et al. | |
| 8,692,075 B2 | 4/2014 | Lemont | |
| 8,766,039 B2 | 7/2014 | Skrsyniarz | |
| 8,772,578 B2* | 7/2014 | Ammerlaan | A01H 5/12 435/410 |
| 8,772,580 B2 | 7/2014 | Holland | |
| 8,809,634 B1 | 8/2014 | Roca et al. | |
| 8,822,763 B2 | 9/2014 | Skrsyniarz | |
| 8,829,281 B2 | 9/2014 | Schryve | |
| 8,847,019 B2 | 9/2014 | Lemont | |

(Continued)

FOREIGN PATENT DOCUMENTS

WO 2000/063432 A1 10/2000

OTHER PUBLICATIONS

Convenience Catalog, accessed online at https://www.rijkzwaan.com/sites/default/files/rijk_zwaan_convenience_catalogus.pdf on Mar. 30, 2020, pp. 1-46.*
Resistance Catalog, accessed online at https://www.rijkzwaan.dk/sites/default/files/bremia_bl._33_en.pdf on Mar. 30, 2020, pp. 1-2.*
Bassett, M. J., "The Role of Leaf Shape in the Inheritance of Heading in Lettuce (*Lactuca sativa* L.)", Journal of the American Society for Horticultural Science, vol. 100, No. 2, 1975, pp. 104-105.
Bennetzen et al., "Approaches and Progress in the Molecular Cloning of Plant Disease Resistance Genes", Genetic Engineering, vol. 14, 1992, pp. 99-124.
Bonnier et al., "New Sources of Major Gene Resistance in Lactuca to Bremia Lactucae", Euphytica, vol. 61, 1992, pp. 203-211.
Debolle et al., "Antimicrobial Peptides from Mirabilis Jalapa and Amaranthus Caudatus: Expression, Processing, Localization and Biological Activity in Transgenic Tobacco", Plant Molecular Biology, vol. 31, 1996, pp. 993-1008.

(Continued)

*Primary Examiner* — Stephen Uyeno
(74) *Attorney, Agent, or Firm* — Morrison & Foerster LLP

(57) ABSTRACT

New lettuce varieties designated 'Ezthana' and 'Eztron' are described. 'Ezthana' and 'Eztron' are lettuce varieties exhibiting stability and uniformity.

18 Claims, 5 Drawing Sheets

(5 of 5 Drawing Sheet(s) Filed in Color)

(56) References Cited

U.S. PATENT DOCUMENTS

| | | | |
|---|---|---|---|
| 8,878,008 B1* | 11/2014 | Votava | A01H 5/12 435/410 |
| 8,957,284 B2 | 2/2015 | Nannes | |
| 8,962,927 B2 | 2/2015 | Nannes | |
| 8,962,928 B2 | 2/2015 | Sinclair | |
| 8,987,559 B2 | 3/2015 | Winsemius | |
| 8,987,560 B2 | 3/2015 | Nannes | |
| 8,993,848 B2 | 3/2015 | Skrsyniarz | |
| 8,993,849 B2 | 3/2015 | Nannes | |
| 8,993,850 B2 | 3/2015 | Lemont | |
| 9,000,268 B2 | 4/2015 | Skrsyniarz | |
| 9,113,609 B2 | 8/2015 | Lemont | |
| 9,179,638 B2 | 11/2015 | Lemont | |
| 9,198,394 B2 | 12/2015 | Holland | |
| 9,277,726 B2 | 3/2016 | Holland | |
| 9,290,774 B2 | 3/2016 | Smits et al. | |
| 9,313,994 B2 | 4/2016 | Skrsyniarz | |
| 9,320,250 B2* | 4/2016 | Ammerlaan | A01H 5/12 |
| 9,332,725 B2 | 5/2016 | Holland | |
| 9,392,765 B2 | 7/2016 | Skrsyniarz | |
| 9,572,321 B2 | 2/2017 | Lemont et al. | |
| 9,635,828 B2 | 5/2017 | Nannes | |
| 9,743,633 B2 | 8/2017 | Holland et al. | |
| 9,814,210 B2* | 11/2017 | Ammerlaan | A01H 5/12 |
| 9,961,873 B2 | 5/2018 | Nannes | |
| 10,015,948 B2 | 7/2018 | Conijn | |
| 10,405,510 B2 | 9/2019 | Vriend | |
| 10,506,773 B2 | 12/2019 | Nannes | |
| 10,517,248 B2 | 12/2019 | Sinclair | |
| 10,542,698 B2 | 1/2020 | Lemont | |
| 10,582,681 B2 | 3/2020 | Sinclair et al. | |
| 2004/0226060 A1 | 11/2004 | Lambalk et al. | |
| 2005/0050596 A1 | 3/2005 | De Jong et al. | |
| 2006/0005272 A1 | 1/2006 | Lambalk et al. | |
| 2009/0193535 A1 | 7/2009 | Ammerlaan | |
| 2009/0271890 A1 | 10/2009 | Lambalk et al. | |
| 2010/0083398 A1 | 4/2010 | Holland et al. | |
| 2010/0299777 A1 | 11/2010 | Lambalk et al. | |
| 2010/0325749 A1 | 12/2010 | Moor et al. | |
| 2011/0078812 A1 | 3/2011 | Holland et al. | |
| 2011/0078813 A1 | 3/2011 | Holland et al. | |
| 2011/0083223 A1 | 4/2011 | Holland et al. | |
| 2011/0167510 A1 | 7/2011 | Lemont et al. | |
| 2011/0191890 A1 | 8/2011 | Ammerlaan | |
| 2011/0197295 A1 | 8/2011 | Schryve | |
| 2011/0277176 A1 | 11/2011 | Conijn et al. | |
| 2011/0296549 A1 | 12/2011 | Holland | |
| 2012/0005771 A1 | 1/2012 | Nannes et al. | |
| 2012/0005772 A1 | 1/2012 | Nannes et al. | |
| 2012/0011611 A1 | 1/2012 | Holland et al. | |
| 2012/0011612 A1 | 1/2012 | Skrsyniarz et al. | |
| 2012/0011613 A1 | 1/2012 | Skrsyniarz et al. | |
| 2012/0042405 A1 | 2/2012 | Lemont et al. | |
| 2012/0042406 A1 | 2/2012 | Lemont et al. | |
| 2012/0073011 A1 | 3/2012 | Conijn et al. | |
| 2012/0073013 A1 | 3/2012 | Argyris | |
| 2012/0096578 A1 | 4/2012 | Van Schijndel | |
| 2012/0222149 A1 | 8/2012 | Nannes et al. | |
| 2013/0024984 A1 | 1/2013 | Skrsyniarz et al. | |
| 2013/0031663 A1 | 1/2013 | Sinclair et al. | |
| 2013/0081149 A1* | 3/2013 | Lemont | A01H 5/12 800/260 |
| 2013/0145504 A1 | 6/2013 | Van Zee | |
| 2013/0219544 A1 | 8/2013 | Van Zee | |
| 2013/0276160 A1 | 10/2013 | Holland et al. | |
| 2013/0298270 A1 | 11/2013 | Skrsyniarz et al. | |
| 2013/0298271 A1 | 11/2013 | Lemont | |
| 2013/0305399 A1 | 11/2013 | Lemont | |
| 2013/0305400 A1 | 11/2013 | Lemont et al. | |
| 2013/0318646 A1 | 11/2013 | Nannes et al. | |
| 2013/0333065 A1 | 12/2013 | Winsemius et al. | |
| 2013/0340106 A1 | 12/2013 | Nannes et al. | |
| 2013/0340107 A1 | 12/2013 | Nannes | |
| 2013/0340108 A1 | 12/2013 | Nannes et al. | |
| 2013/0340109 A1 | 12/2013 | Skrsyniarz et al. | |
| 2014/0013463 A1 | 1/2014 | Garcia | |
| 2014/0033339 A1 | 1/2014 | Skrsyniarz et al. | |
| 2014/0041069 A1 | 2/2014 | Nannes et al. | |
| 2014/0041070 A1 | 2/2014 | Vriend | |
| 2014/0053289 A1 | 2/2014 | Sinclair et al. | |
| 2014/0065286 A1 | 3/2014 | Moor et al. | |
| 2014/0259193 A1 | 9/2014 | Lemont et al. | |
| 2014/0259194 A1 | 9/2014 | Lemont et al. | |
| 2014/0283159 A1 | 9/2014 | Lemont et al. | |
| 2014/0283161 A1 | 9/2014 | Holland et al. | |
| 2015/0020225 A1 | 1/2015 | Holland et al. | |
| 2015/0135356 A1 | 5/2015 | Smits et al. | |
| 2015/0150154 A1 | 5/2015 | Holland | |
| 2015/0164035 A1 | 6/2015 | Skrsyniarz et al. | |
| 2015/0289469 A1 | 10/2015 | Holland | |
| 2015/0373942 A1 | 12/2015 | Skrsyniarz | |
| 2016/0157455 A1 | 6/2016 | Nannes | |
| 2016/0198670 A1 | 7/2016 | Lemont et al. | |
| 2017/0099800 A1 | 4/2017 | Holland et al. | |
| 2017/0142925 A1 | 5/2017 | Nannes et al. | |
| 2017/0251622 A1 | 9/2017 | Sinclair et al. | |
| 2017/0258029 A1 | 9/2017 | Conijn et al. | |
| 2018/0228112 A1 | 8/2018 | Nannes | |
| 2018/0242548 A1 | 8/2018 | Lemont | |
| 2018/0249669 A1 | 9/2018 | Sinclair | |
| 2018/0303054 A1 | 10/2018 | Vriend | |
| 2019/0029211 A1 | 1/2019 | Lemont | |
| 2019/0053456 A1 | 2/2019 | Lemont | |
| 2019/0191652 A1 | 6/2019 | Sinclair | |
| 2019/0335697 A1 | 11/2019 | Vriend et al. | |
| 2020/0053972 A1 | 2/2020 | Sinclair | |
| 2020/0084988 A1 | 3/2020 | Winsemius | |

OTHER PUBLICATIONS

Devries et al., "Numerical Morphological Analysis of Lettuce Cultivars and Species (*Lactuca* Sect. *Lactuca, asteraceae*)", Plant Systematics and Evolution, vol. 193, 1994, pp. 125-141.

Dufresne et al., "Genetic Sequences: How are they Patented?", Nature Biotechnology, vol. 22, No. 2, Feb. 2004, pp. 231-232.

Eshed et al., "Less-Than-Additive Epistatic Interactions of Quantitative Trait Loci in Tomato", Genetics, vol. 143, Aug. 1996, pp. 1807-1817.

Farrara et al., "Genetic Analysis of Factors for Resistance to Downy Mildew (*Bremia lactucae*) in Species of Lettuce (*Lactuca sativa* and *L. Serriola*)", Plant Pathology, vol. 36, 1987, pp. 499-514.

Farrara et al., "Identification of New Sources of Resistance to Downy Mildew in *Lactuca* Spp.", HortScience, vol. 22, No. 4, Aug. 1987, pp. 647-649.

Kessell et al., "Recessive Resistance to Plasmopara Lactucae-Radicis Maps by Bulked Segregant Analysis to a Cluster of Dominant Disease Resistance Genes in Lettuce", Molecular Plant-Microbe Interactions, vol. 6. No. 6, 1993, pp. 722-728.

Kraft et al., "Linkage Disequilibrium and Fingerprinting in Sugar Beet", Theor. Appl. Genet., vol. 101, 2000, pp. 323-326.

Landry et al., "A Genetic Map of Lettuce (*Lactuca sativa* L.) with Restriction Fragment Length Polymorphism, Isozyme, Disease Resistance and Morphological Markers", Genetics, vol. 116, Jun. 1987, pp. 331-337.

Lebeda et al., "Further Investigation of the Specificity Between Wild Lactuca of Interactions Spp. and Bremia Lactucae Isolates from Lactuca Serriola", Journal of Phytopathology, vol. 133, 1991, pp. 57-64.

Lemont, Magali, U.S. Unpublished Patent Application No. 16/103,776, filed on Aug. 14, 2018, titled "Lettuce Varieties 'Ardeor', 'Advisor', and 'Jokary'", (Copy Not Attached).

Lemont, Magali, U.S. Appl. No. 16/049,722, filed Jul. 30, 2018, titled "Lettuce Varieties 'Cavendish', 'Clearwater', and 'Pensacola'", (Copy Not Attached).

Maisonneuve et al., "Rapid Mapping of Two Genes for Resistance to Downy Mildew from Lactuca Seniote to Existing Clusters of Resistance Genes", Theor Appl Genet, vol. 89, 1994, pp. 96-104.

Maisonneuve et al., "Sexual and Somatic Hybridization in the Genus *Lactuca*", Euphytica, vol. 85, 1995, pp. 281-285.

(56) References Cited

OTHER PUBLICATIONS

Maisonneuve et al., "Inheritance of Resistance to Beet Western Yellows Virus in *Lactuca virosa* L.", Hortscience, vol. 26, No. 12, Dec. 1991, pp. 1543-1545.

Maisonneuve, Brigitte, "Lactuca Virosa, a Source of Disease Resistance Genes for Lettuce Breeding: Results and Difficulties for Gene Introgression", Eucarpia Leafy Vegetables, 2003, pp. 61-67.

Maisonneuve, Brigitte, "Utilisation De La Culture in Vitro D'embryons Immatures Pour Les Croisements Interspecifíques Entre *Lactuca sativa* L. et L. *Saligna* L. ou L. *Virosa* L.; Etude Des Hybrides Obtenus", ("Interspecific hybridization in *Lactuca* sp. using in vitro culture of immature embryos, and study of hybrid offspring" Agronomie, vol. 7, No. 5 (The summary is in English), 1987, pp. 313-319.

Michelmore et al., "Clusters of Resistance Genes in Plants Evolve by Divergent Selection and a Birth-and-Death Process", Genome Research, vol. 8, 1998, pp. 1113-1130.

Michelmore et al., "Molecular Markers and Genome Analysis in the Manipulation of Lettuce Downy Mildew", Advances in Molecular Genetics of Plant-Microbe Interactions, 1993, pp. 517-523.

Michelmore et al., "The Inheritance of Virulence in Bremia lactucae to Match Resistance Factors 3 4,5,6,8,9,10 and 11 in lettuce (*Lactuca sativa*)", Plant Pathology, vol. 33, 1984, pp. 301-315.

Michelmore et al., "Transformation of Lettuce (*Lactuca sativa*) Mediated by Agrobacterium Tumefaciens", Plant Cell Rep, vol. 6, 1987, pp. 439-442.

Pang et al., "Expression of a Gene Encoding a Scorpion Insectotoxin Peptide in Yeast, Bacteria and Plants", Gene, vol. 116, 1992, pp. 165-172.

Paran et al., "Development of Reliable PCR-Based Markers Linked to Downy Mildew Resistance Genes in Lettuce", Theory of Applied Genetics, vol. 85, 1993, pp. 985-993.

Paran et al., "Identification of Restriction Fragment Length Polymorphism and Random Amplified Polymorphic DNA Markers Linked to Downy Mildew Resistance Genes in Lettuce, Using Near-Isogenic Lines", Genome, vol. 34, 1991, pp. 1021-1027.

Ryder et al., "Inheritance and Epistasis Studies of Chlorophyll Deficiency in Lettuce", J. Amer. Soc. Hort. Sci., vol. 124, No. 6, 1999, pp. 636-640.

Ryder et al., "Lettuce Genetics: Inheritance, Linkage and Epistasis", J. Amer. Soc. Hort. Sci., vol. 117, No. 3, 1992, pp. 504-507.

Stam, Piet, "Construction of Integrated Genetic Linkage Maps by Means of a New Computer Package: JoinMap", The Plant Journal, vol. 3, No. 5, 1993, pp. 739-744.

Thomas et al., "Lettuce Production in the United States", In Agriculture Handbook No 221. Agricultural Research Service of the United States Department of Aquiculture, 1974, 3 pages.

Vriend et al., U.S. Appl. No. 15/947,694, filed Apr. 6, 2018, titled "Lettuce Varieties 'Ezuma' and 'Giralda'", (Copy Not Attached).

Waycott et al., "Differentiation of Nearly Identical Germplasm Accessions by a Combination of Molecular and Morphologic Analyses", Genome, vol. 37, 1994, pp. 577-583.

Williams et al., "DNA Polymorphisms Amplified by Arbitrary Primers are useful as Genetic Markers", Nucleic Acids Research, vol. 18, No. 22, 1990, pp. 6531-6535.

Xinrun et al., "Genotypic Effects on Tissue Culture Response of Lettuce Cotyledons", J. Genet. & Breed., vol. 46, 1992, pp. 287-290.

Enza Zaden USA, Inc. Jan. 2020. 'Burgandy'. Vegetable Seed Catalogue USA & Canada 2020. Available online at <https://webkiosk.enzazaden.com/catalogue-usa-2020/62983894>, Obtained on Jun. 25, 2020. p. 13.

Enza Zaden USA, Inc. Jan. 2020. 'Ezthana' and 'Eztron'. Vegetable Seed Catalogue USA & Canada 2020. Available online at <https://webkiosk.enzazaden.com/catalogue-usa-2020/62983894>, Obtained on Jun. 25, 2020. p. 12.

Enza Zaden. Aug. 2019. 'Burgandy'. Hydroponic 2019 Brochure: Lettuce Endive Herbs. Available online at <https://webkiosk.enzazaden.com/hydroponic-international-2019/62782367>, Obtained on Jun. 25, 2020. p. 34.

Enza Zaden. 'Brentwood'. 2019 Vegetable Seed Catalog USA & Canada. Available online at <http://www.enzazaden.us/products-and-services/our-products/Brentwood> Obtained on Jun. 21, 2019. 2 pages.

Enza Zaden. 'Burgandy'. Products & Services. Available online at <https://www.enzazaden.com/us/products-and-services/our-products/Burgandy>, Obtained on Jun. 25, 2020. 1 page.

Enza Zaden. 'Marciano'. Products & Services. Available online at <https://www.enzazaden.com/us/products-and-services/our-products/Marciano>, Obtained on Jun. 30, 2020. 1 page.

Enza Zaden. Nov. 2019. 'Iblea'. Lattuga 2020 Brochure, Italy, p. 17. Available online at <https://webkiosk.enzazaden.com/brochure-lattuga-2019/62735861/3>, Obtained on Mar. 23, 2020. 2 pages. English Translation Included.

Enza Zaden. Sep. 2019. 'Iblea'. Products and Services Italy. Available online at <https://www.enzazaden.com/it/products-and-services/our-products/Iblea>, Obtained on Mar. 23, 2020. 2 pages. English Translation Included.

Enza Zaden. 'Somerset'. 2019 Seed Catalog. Available online at <http://www.enzazaden.us/products-and-services/our-products/Somerset> Obtained on May 6, 2019. 1 page.

U.S. Appl. No. 16/745,149, filed Jan. 16, 2020, titled "Lettuce Varieties 'Kalista' and 'Ezbruke'," (Copy not submitted herewith pursuant to the waiver of 37 C.F.R. § 1.98(a)(2)(iii)).

U.S. Appl. No. 16/909,346, filed Jun. 23, 2020, titled "Lettuce Variety 'Clearwater'," (Copy not submitted herewith pursuant to the waiver of 37 C.F.R. § 1.98(a)(2)(iii)).

* cited by examiner

LETTUCE VARIETIES 'EZTHANA' AND 'EZTRON'

CROSS-REFERENCE TO RELATED APPLICATION

This application claims the benefit of U.S. Provisional Application No. 62/508,208, filed May 18, 2017, which is hereby incorporated by reference in its entirety.

FIELD OF THE INVENTION

The present invention relates to the field of plant breeding. In particular, this invention relates to a new lettuce, *Lactuca sativa* varieties designated 'Ezthana' and 'Eztron'.

BACKGROUND OF THE INVENTION

Cultivated forms of lettuce belong to the highly polymorphic species *Lactuca sativa* that is grown for its edible head and leaves. As a crop, lettuce is grown commercially wherever environmental conditions permit the production of an economically viable yield. For planting purposes, the lettuce season is typically divided into three categories (i.e., early, mid, and late), with coastal areas planting from January to August, and desert regions planting from August to December. Fresh lettuce is consumed nearly exclusively as fresh, raw product and occasionally as a cooked vegetable.

*Lactuca sativa* is in the Cichorieae tribe of the Asteraceae (Compositae) family. Lettuce is related to chicory, sunflower, aster, dandelion, artichoke, and chrysanthemum. *Sativa* is one of about 300 species in the genus *Lactuca*. There are seven different morphological types of lettuce. The crisphead group includes the iceberg and batavian types. Iceberg lettuce has a large, firm head with a crisp texture and a white or creamy yellow interior. The batavian lettuce predates the iceberg type and has a smaller and less firm head. The butterhead group has a small, soft head with an almost oily texture. The romaine, also known as cos lettuce, has elongated upright leaves forming a loose, loaf-shaped head and the outer leaves are usually dark green. Leaf lettuce, also known as cutting lettuce, comes in many varieties, none of which form a head, and include the green oak leaf variety. Latin lettuce looks like a cross between romaine and butterhead. Stem lettuce has long, narrow leaves and thick, edible stems. Oilseed lettuce is a type grown for its large seeds that are pressed to obtain oil.

Lettuce is an increasingly popular crop. Worldwide lettuce consumption continues to increase. As a result of this demand, there is a continued need for new lettuce varieties. In particular, there is a need for improved crisp lettuce varieties that are stable, high yielding, and agronomically sound.

SUMMARY OF THE INVENTION

In order to meet these needs, the present invention is directed to improved lettuce varieties.

In one embodiment, the present invention is directed to a lettuce, *Lactuca sativa*, seed designated as 'Ezthana', representative sample of seed having been deposited under NCIMB Accession Number 43135. In one embodiment, the present invention is directed to a *Lactuca sativa* lettuce plant and parts isolated therefrom produced by growing 'Ezthana' lettuce seed. In another embodiment, the present invention is directed to a *Lactuca sativa* plant and parts isolated therefrom having all the physiological and morphological characteristics of a *Lactuca sativa* plant produced by growing 'Ezthana' lettuce seed having NCIMB Accession Number 43135. In still another embodiment, the present invention is directed to an $F_1$ hybrid *Lactuca sativa* lettuce seed, plants grown from the seed, and a head isolated therefrom having 'Ezthana' as a parent, where 'Ezthana' is grown from 'Ezthana' lettuce seed having NCIMB Accession Number 43135.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Ezthana' lettuce plants. In another embodiment, the present invention is further directed to tissue culture of 'Ezthana' lettuce plants, and to lettuce plants regenerated from the tissue culture, where the plant has all of the morphological and physiological characteristics of 'Ezthana' lettuce plants.

In still another embodiment, the present invention is further directed to packaging material containing 'Ezthana' plant parts. Such packaging material includes but is not limited to boxes, plastic bags, etc. The 'Ezthana' plant parts may be combined with other plant parts of other plant varieties.

In yet another embodiment, the present invention is further directed to a method of selecting lettuce plants, by a) growing 'Ezthana' lettuce plants where the 'Ezthana' plants are grown from lettuce seed having NCIMB Accession Number 43135 and b) selecting a plant from step a). In another embodiment, the present invention is further directed to lettuce plants, plant parts and seeds produced by the lettuce plants where the lettuce plants are isolated by the selection method of the invention.

In another embodiment, the present invention is further directed to a method of breeding lettuce plants by crossing a lettuce plant with a plant grown from 'Ezthana' lettuce seed having NCIMB Accession Number 43135. In still another embodiment, the present invention is further directed to lettuce plants, lettuce parts from the lettuce plants, and seeds produced therefrom where the lettuce plant is isolated by the breeding method of the invention.

In another embodiment, the present invention is directed to methods for producing a male sterile lettuce plant by introducing a nucleic acid molecule that confers male sterility into a lettuce plant produced by growing 'Ezthana' lettuce seed, and to male sterile lettuce plants produced by such methods.

In another embodiment, the present invention is directed to methods of producing an herbicide resistant lettuce plant by introducing a gene conferring herbicide resistance into a lettuce plant produced by growing 'Ezthana' lettuce seed, where the gene confers resistance to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant lettuce plants produced by such methods.

In another embodiment, the present invention is directed to methods of producing a pest or insect resistant lettuce plan by introducing a gene conferring pest or insect resistance into a lettuce plant produced by growing 'Ezthana' lettuce seed, and to pest or insect resistant lettuce plants produced by such methods. In certain embodiments, the gene conferring pest or insect resistance encodes a *Bacillus thuringiensis* endotoxin.

In another embodiment, the present invention is directed to methods of producing a disease resistant lettuce plant by introducing a gene conferring disease resistance into a lettuce plant produced by growing 'Ezthana' lettuce seed, and to disease resistant lettuce plants produced by such methods.

In another embodiment, the present invention is directed to methods of producing a lettuce plant with a value-added trait by introducing a gene conferring a value-added trait into a lettuce plant produced by growing 'Ezthana' lettuce seed, where the gene encodes a protein selected from a ferritin, a nitrate reductase, and a monellin. Certain embodiments are also directed to lettuce plants having a value-added trait produced by such methods.

In another embodiment, the present invention is directed to methods of introducing a desired trait into lettuce variety 'Ezthana', by: (a) crossing a 'Ezthana' plant, where a sample of 'Ezthana' lettuce seed was deposited under NCIMB Accession Number 43135, with a plant of another lettuce variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a 'Ezthana' plant to produce backcross progeny plants; (d) selecting for backcross progeny plants that have the desired trait and all of the physiological and morphological characteristics of lettuce variety 'Ezthana'; and (e) repeating steps (c) and (d) two or more times in succession to produce selected third or higher backcross progeny plants that comprise the desired trait. Certain embodiments are also directed to lettuce plants produced by such methods, where the plants have the desired trait and all of the physiological and morphological characteristics of lettuce variety 'Ezthana'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile.

In another embodiment, the present invention provides for single gene converted plants of 'Ezthana'. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage.

In one embodiment, the present invention is directed to lettuce, *Lactuca sativa*, seed designated as 'Eztron' having NCIMB Accession Number 43136. In one embodiment, the present invention is directed to a *Lactuca sativa* lettuce plant and parts isolated therefrom produced by growing 'Eztron' lettuce seed. In another embodiment, the present invention is directed to a *Lactuca sativa* plant and parts isolated therefrom having all the physiological and morphological characteristics of a *Lactuca sativa* plant produced by growing 'Eztron' lettuce seed having NCIMB Accession Number 43136. In still another embodiment, the present invention is directed to an $F_1$ hybrid *Lactuca sativa* lettuce seed, plants grown from the seed, and a head isolated therefrom having 'Eztron' as a parent, where 'Eztron' is grown from 'Eztron' lettuce seed having NCIMB Accession Number 43136.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Eztron' lettuce plants. In another embodiment, the present invention is further directed to tissue culture of 'Eztron' lettuce plants, and to lettuce plants regenerated from the tissue culture, where the plant has all of the morphological and physiological characteristics of 'Eztron' lettuce plants.

In still another embodiment, the present invention is further directed to packaging material containing 'Eztron' plant parts. Such packaging material includes but is not limited to boxes, plastic bags, etc. The 'Eztron' plant parts may be combined with other plant parts of other plant varieties.

In yet another embodiment, the present invention is further directed to a method of selecting lettuce plants, by a) growing 'Eztron' lettuce plants where the 'Eztron' plants are grown from lettuce seed having NCIMB Accession Number 43136 and b) selecting a plant from step a). In another embodiment, the present invention is further directed to lettuce plants, plant parts and seeds produced by the lettuce plants where the lettuce plants are isolated by the selection method of the invention.

In another embodiment, the present invention is further directed to a method of breeding lettuce plants by crossing a lettuce plant with a plant grown from 'Eztron' lettuce seed having NCIMB Accession Number 43136. In still another embodiment, the present invention is further directed to lettuce plants, lettuce parts from the lettuce plants, and seeds produced therefrom where the lettuce plant is isolated by the breeding method of the invention.

In another embodiment, the present invention is directed to methods for producing a male sterile lettuce plant by introducing a nucleic acid molecule that confers male sterility into a lettuce plant produced by growing 'Eztron' lettuce seed, and to male sterile lettuce plants produced by such methods.

In another embodiment, the present invention is directed to methods of producing an herbicide resistant lettuce plant by introducing a gene conferring herbicide resistance into a lettuce plant produced by growing 'Eztron' lettuce seed, where the gene confers resistance to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant lettuce plants produced by such methods.

In another embodiment, the present invention is directed to methods of producing a pest or insect resistant lettuce plan by introducing a gene conferring pest or insect resistance into a lettuce plant produced by growing 'Eztron' lettuce seed, and to pest or insect resistant lettuce plants produced by such methods. In certain embodiments, the gene conferring pest or insect resistance encodes a *Bacillus thuringiensis* endotoxin.

In another embodiment, the present invention is directed to methods of producing a disease resistant lettuce plant by introducing a gene conferring disease resistance into a lettuce plant produced by growing 'Eztron' lettuce seed, and to disease resistant lettuce plants produced by such methods.

In another embodiment, the present invention is directed to methods of producing a lettuce plant with a value-added trait by introducing a gene conferring a value-added trait into a lettuce plant produced by growing 'Eztron' lettuce seed, where the gene encodes a protein selected from a ferritin, a nitrate reductase, and a monellin. Certain embodiments are also directed to lettuce plants having a value-added trait produced by such methods.

In another embodiment, the present invention is directed to methods of introducing a desired trait into lettuce variety 'Eztron', by: (a) crossing a 'Eztron' plant, where a sample of 'Eztron' lettuce seed was deposited under NCIMB Accession Number 43136, with a plant of another lettuce variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a 'Eztron' plant to produce backcross progeny plants; (d) selecting for backcross progeny plants that have the desired trait and all of the physiological and morphological characteristics of lettuce variety 'Eztron'; and (e) repeating steps (c) and (d) two or more times in succession to produce selected third or higher backcross progeny plants that comprise the desired trait. Certain embodiments are also directed to lettuce plants produced by such methods, where the plants have the desired trait and all of the physiological and morphological characteristics of lettuce variety 'Eztron'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile.

In another embodiment, the present invention provides for single gene converted plants of 'Eztron'. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage.

In a further embodiment, the present invention relates to methods for developing lettuce plants in a lettuce plant breeding program using plant breeding techniques including recurrent selection, backcrossing, pedigree breeding, restriction fragment length polymorphism enhanced selection, and genetic marker enhanced selection. Seeds, lettuce plants, and parts thereof, produced by such breeding methods are also part of the invention.

In addition to the exemplary aspects and embodiments described above, further aspects and embodiments will become apparent by reference by study of the following description.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 3A shows leaves of lettuce variety 'Ezthana'. FIG. 3B shows leaves of lettuce variety 'Eztron'. FIG. 3C shows leaves of lettuce variety 'Experience'.

DETAILED DESCRIPTION OF THE INVENTION

Figure 1A:
FIG. 1A shows a side view of leaves of lettuce variety 'Ezthana'.

There are numerous steps in the development of novel, desirable lettuce germplasm. Plant breeding begins with the analysis of problems and weaknesses of current lettuce germplasms, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

Choice of breeding or selection methods can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended, etc.).

Promising advanced breeding lines may be thoroughly tested and compared to appropriate standards in environments representative of the commercial target area(s) for at least three years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made.

One goal of lettuce plant breeding is to develop new, unique, and genetically superior lettuce varieties. A breeder can initially select and crosses two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial lettuce varieties thus requires the development of parental lettuce varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

In some embodiments, the single-seed descent procedure may refer to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs, which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into lettuce varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Additional non-limiting examples of breeding methods that may be used include, without limitation, those found in *Principles of Plant Breeding*, John Wiley and Son, pp. 115-161 (1960); Allard (1960); Simmonds (1979); Sneep, et al. (1979); Fehr (1987); and "Carrots and Related Vegetable Umbelliferae," Rubatzky, V. E., et al. (1999).

Definitions

In the description that follows, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Big Vein virus. Big vein is a disease of lettuce caused by Lettuce Mirafiori Big Vein Virus which is transmitted by the fungus *Olpidium virulentus*, with vein clearing and leaf shrinkage resulting in plants of poor quality and reduced marketable value.

Bolting. The premature development of a flowering stalk, and subsequent seed, before a plant produces a food crop. Bolting is typically caused by late planting.

*Bremia lactucae*. An oomycete that causes downy mildew in lettuce in cooler growing regions.

Core length. Length of the internal lettuce stem measured from the base of the cut and trimmed head to the tip of the stem.

Corky root. A disease caused by the bacterium *Sphingomonas suberifaciens*, which causes the entire taproot to become brown, severely cracked, and non-functional.

Cotyledon. One of the first leaves of the embryo of a seed plant; typically one or more in monocotyledons, two in dicotyledons, and two or more in gymnosperms.

Essentially all the physiological and morphological characteristics. A plant having essentially all the physiological and morphological characteristics means a plant having the physiological and morphological characteristics of the recurrent parent, except for the characteristics derived from the converted gene.

First water date. The date the seed first receives adequate moisture to germinate. This can and often does equal the planting date.

Gene. As used herein, "gene" refers to a segment of nucleic acid. A gene can be introduced into a genome of a species, whether from a different species or from the same species, using transformation or various breeding methods.

Head diameter. Diameter of the cut and trimmed head, sliced vertically, and measured at the widest point perpendicular to the stem.

Head height. Height of the cut and trimmed head, sliced vertically, and measured from the base of the cut stem to the cap leaf.

Head weight. Weight of saleable lettuce head, cut and trimmed to market specifications.

Lettuce Mosaic virus. A disease that can cause a stunted, deformed, or mottled pattern in young lettuce and yellow, twisted, and deformed leaves in older lettuce.

Maturity date. Maturity refers to the stage when the plants are of full size or optimum weight, in marketable form or shape to be of commercial or economic value.

*Nasonovia ribisnigri*. A lettuce aphid that colonizes the innermost leaves of the lettuce plant, contaminating areas that cannot be treated easily with insecticides.

Quantitative Trait Loci. Quantitative Trait Loci (QTL) refers to genetic loci that control to some degree, numerically representable traits that are usually continuously distributed.

Ratio of head height/diameter. Head height divided by the head diameter is an indication of the head shape; <1 is flattened, 1=round, and >1 is pointed.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Single gene converted. Single gene converted or conversion plant refers to plants which are developed by a plant breeding technique called backcrossing or via genetic engineering where essentially all of the desired morphological and physiological characteristics of a line are recovered in addition to the single gene transferred into the line via the backcrossing technique or via genetic engineering.

Tip burn. Means a browning of the edges or tips of lettuce leaves that is a physiological response to a lack of calcium.

Wet date. The wet date corresponds to the first planting date of lettuce.

Overview of the Variety 'Ezthana'

Figure 1B:
FIG. 1B shows a top view of leaves of lettuce variety 'Ezthana'.

Lettuce variety 'Ezthana' is a dark green colored cutting (i.e., leaf) lettuce variety that is early bolting with a small plant diameter, upright growth, and leaves that are thick and narrow elliptic in shape in three dimensions. 'Ezthana' has a growing season that includes spring, summer, and autumn, and is suitable for cultivation in the open. Additionally, lettuce variety 'Ezthana' is resistant to *Bremia lactucae* (downy mildew) strains Bl:16-Bl:33; resistant to *Nasonovia ribisnigri* biotype Nr:0; resistant to lettuce mosaic virus (LMV) strain Ls-1; and resistant to lettuce dieback (TBSV). FIGS. 1A and 1B depict leaves of lettuce variety 'Ezthana'. Lettuce variety 'Ezthana' is the result of numerous generations of plant selections chosen for its plant upright growth, and its resistance to pests and diseases.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Ezthana'.

Objective Description of the Variety 'Ezthana'

Figure 3A:
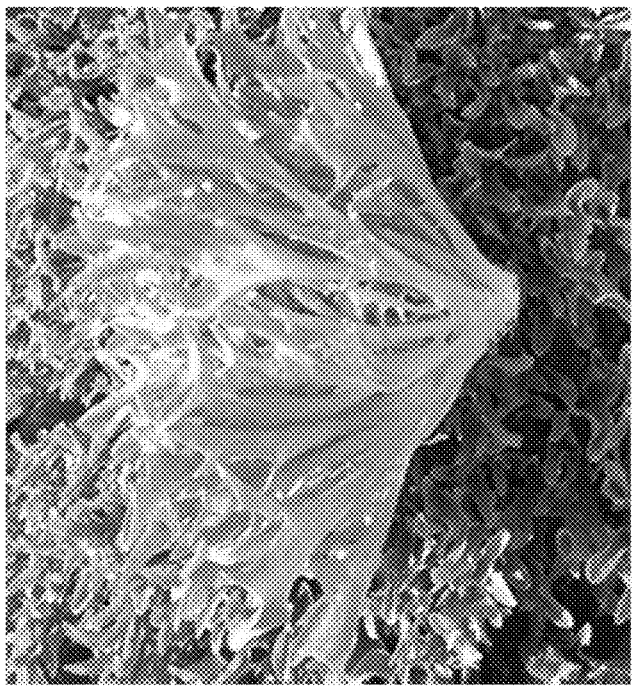
FIGS. 3A, 3B, and 3C show a comparison between lettuce varieties 'Ezthana', 'Eztron', and 'Experience'.
Figure 3B:
Figure 3C:
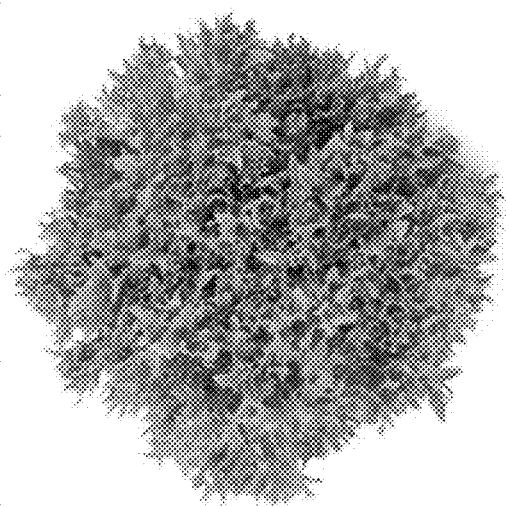

Lettuce variety 'Ezthana' has the following morphologic and other characteristics:
  Plant:
    Type: Cutting
    Diameter: Small
  Seed:
    Color: Black
  Mature Leaves:
    Margin:
      Hue of green color of outer leaves: Absent
      Intensity of color of outer leaves: Dark
    Anthocyanin coloration: Absent
  Leaf:
    Attitude at harvest maturity: Erect
    Blade: Degree of undulation of margin: Weak
    Density of incisions on margin on apical part of leaf blade: Medium to dense
    Color: Dark green
    Shape: Narrow elliptic
    Thickness: Thick
  Axillary sprouting: Very weak to weak
  Bolting:
    Class: Early
  Disease/Pest Resistance:
    Lettuce mosaic virus (LMV) strain Ls-1: Resistant
    Lettuce dieback (TB SV): Resistant
    Downy Mildew (*Bremia lactucae*): Resistant to Bl:16-Bl:33
  Pests:
    *Nasonovia ribisnigri* biotype 0 (Nr:0): Resistant Comparisons to Other Lettuce Varieties Table 1 below compares characteristics of lettuce variety 'Ezthana' with the lettuce variety 'Experience'. Column 1 lists the characteristics, column 2 shows the characteristics for lettuce variety 'Ezthana', and column 3 shows the characteristics for lettuce variety 'Experience'. Further distinguishing features are apparent from the comparison of the two varieties depicted in FIGS. 3A and 3C.

TABLE 1

| Characteristic | 'Ezthana' | 'Experience' |
|---|---|---|
| Leaf color | Dark green | Blond |
| Density of incisions on margin on apical part of leaf blade | Medium to dense | Medium |
| Leaf thickness | Thick | Medium |
| Leaf shape | Narrow elliptic | Obovate |
| Plant diameter | Small | Medium |
| Leaf: Attitude at harvest maturity | Erect | Semi-erect |
| Leaf blade: Degree of undulation of margin | Weak | Medium |
| Axillary sprouting | Very weak to weak | Weak |

Table 2 below compares characteristics of lettuce variety 'Ezthana' with the lettuce variety 'Eztron'. Column 1 lists the characteristics, column 2 shows the characteristics for lettuce variety 'Ezthana', and column 3 shows the characteristics for lettuce variety 'Eztron'. Further distinguishing features are apparent from the comparison of the two varieties depicted in FIGS. 3A and 3B.

TABLE 2

| Characteristic | 'Ezthana' | 'Eztron' |
|---|---|---|
| Plant diameter | Small | Medium |
| Leaf shape | Narrow elliptic | Broad obtrullate |
| Density of incisions on margin on apical part of leaf blade | Medium to dense | Medium |
| Leaf color | Dark green | Green |
| Leaf thickness | Thick | Medium |

Overview of the Variety 'Eztron'

Figure 2A:
FIG. 2A shows top view and side view of leaves of lettuce variety 'Eztron'.
Figure 2B:
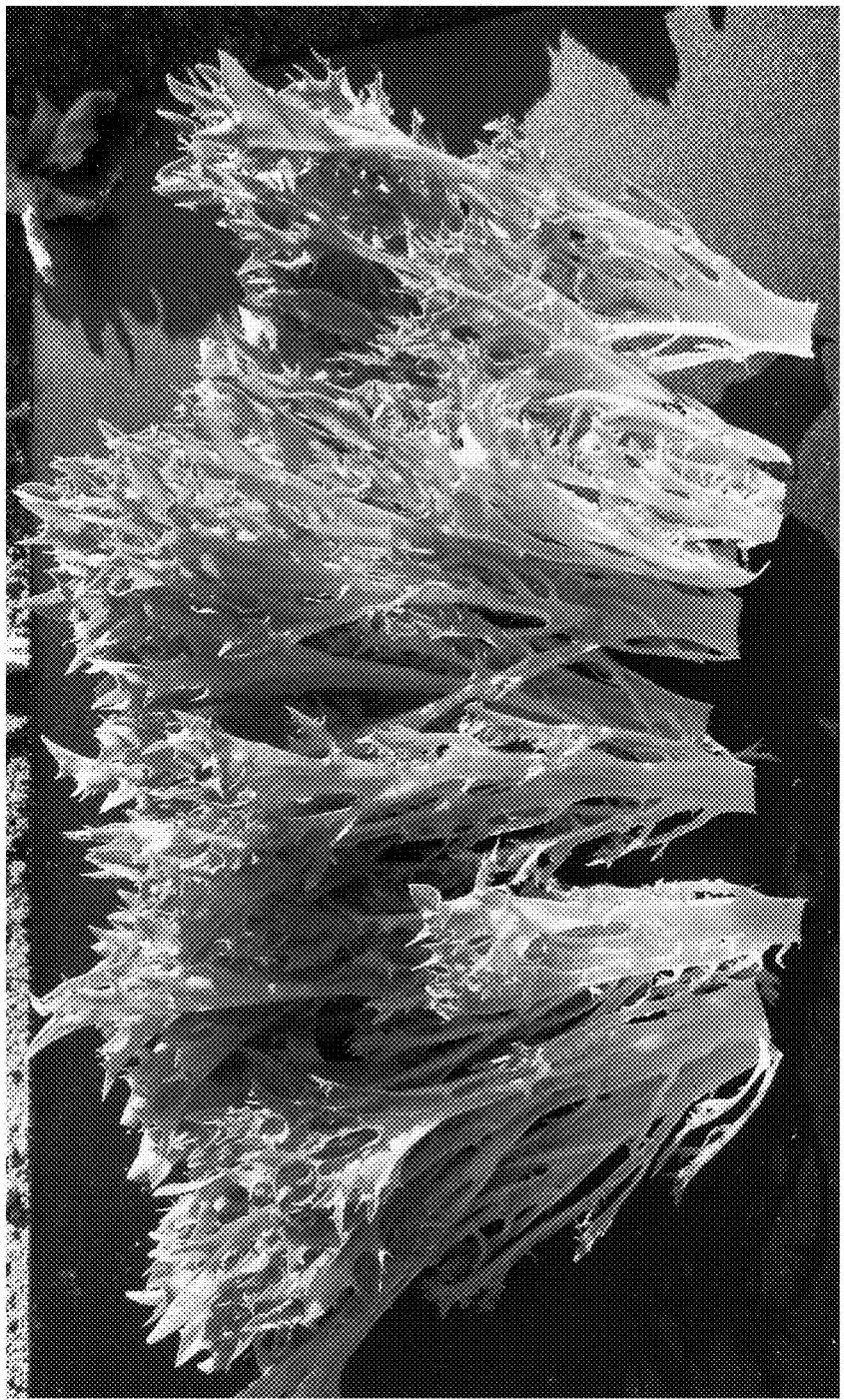
FIG. 2B shows side view of leaves of lettuce variety 'Eztron'.

Lettuce variety 'Eztron' is a medium green colored cutting (i.e., leaf) lettuce variety that is medium bolting with a medium plant diameter, broad obtrullate leaf shape with very small cutting surface, and medium to dense leaf blade density. 'Eztron' has a growing season that includes spring, summer, and autumn, and is suitable for cultivation in the open. Additionally, lettuce variety 'Eztron' is resistant to *Bremia lactucae* (downy mildew) strains Bl:16-Bl:33; resistant to *Nasonovia ribisnigri* biotype Nr:0; resistant to lettuce mosaic virus (LMV) strain Ls-1; and resistant to lettuce dieback (TBSV). FIGS. 2A and 2B depict leaves of lettuce variety 'Eztron'. Lettuce variety 'Eztron' is the result of numerous generations of plant selections chosen for its plant size, head size, leaf shape, and its resistance to pests and diseases.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Eztron'.

Objective description of the variety 'Eztron'

Lettuce variety 'Eztron' has the following morphologic and other characteristics:

Plant:
　Type: Cutting
　Diameter: Medium
Seed:
　Color: Black
Mature Leaves:
　Margin:
　　Hue of green color of outer leaves: Absent
　　Intensity of color of outer leaves: Medium
　　Anthocyanin coloration: Absent
　Leaf:
　　Color: Green
　　Shape: Broad obtrullate
　　Density of incisions on margin on apical part of leaf blade: Medium
　　Thickness: Medium
　　Blistering: Absent to very weak
　Axillary sprouting: Very weak to weak
　Head:
　　Density: Medium to dense
　Bolting:
　　Class: Medium
　Disease/Pest Resistance:
　　Lettuce mosaic virus (LMV) strain Ls-1: Resistant
　　Lettuce dieback (TBSV): Resistant
　　Downy Mildew (*Bremia lactucae*): Resistant to Bl:16-Bl:33
　Pests:
　　*Nasonovia ribisnigri* biotype 0 (Nr:0): Resistant Comparisons to Other Lettuce Varieties Table 3 below compares characteristics of lettuce variety 'Eztron' with the lettuce variety 'Experience'. Column 1 lists the characteristics, column 2 shows the characteristics for lettuce variety 'Eztron', and column 3 shows the characteristics for lettuce variety 'Experience'. Further distinguishing features are apparent from the comparison of the two varieties depicted in FIGS. 3B and 3C.

TABLE 3

| Characteristic | 'Eztron' | 'Experience' |
|---|---|---|
| Leaf color | Green | Blond |
| Leaf shape | Broad obtrullate | Obovate |
| Leaf: Blistering | Absent to very weak | Weak |
| Axillary sprouting | Very weak to weak | Weak |
| Head: Density | Medium to dense | Medium |
| Time of beginning of bolting under long day conditions | Medium | Late |

Table 4 below compares characteristics of lettuce variety 'Eztron' with the lettuce variety 'Ezthana'. Column 1 lists the characteristics, column 2 shows the characteristics for lettuce variety 'Eztron', and column 3 shows the characteristics for lettuce variety 'Ezthana'. Further distinguishing features are apparent from the comparison of the two varieties depicted in FIGS. 3A and 3B.

TABLE 4

| Characteristic | 'Eztron' | 'Ezthana' |
|---|---|---|
| Plant diameter | Medium | Small |
| Leaf shape | Broad obtrullate | Narrow elliptic |
| Density of incisions on margin on apical part of leaf blade | Medium | Medium to dense |

TABLE 4-continued

| Characteristic | 'Eztron' | 'Ezthana' |
|---|---|---|
| Leaf color | Green | Dark green |
| Leaf thickness | Medium | Thick |

Further Embodiments
Gene Conversions

When the term "lettuce plant" is used in the context of the present invention, this also includes any gene conversions of that variety. The term "gene converted plant" as used herein refers to those lettuce plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental lettuce plant which contributes the gene for the desired characteristic is termed the "nonrecurrent" or "donor parent." This terminology refers to the fact that the nonrecurrent parent is used one time in the backcross protocol and therefore does not recur. The parental lettuce plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a lettuce plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212, the disclosures of which are specifically hereby incorporated by reference.

Tissue Culture

Further reproduction of the variety can occur by tissue culture and regeneration. Tissue culture of various tissues of lettuce and regeneration of plants therefrom is well known and widely published. For example, reference may be had to Teng, et al., *HortScience,* 27:9, 1030-1032 (1992); Teng, et al., *HortScience,* 28:6, 669-1671 (1993); Zhang, et al., *Journal of Genetics and Breeding,* 46:3, 287-290 (1992); Webb, et al., *Plant Cell Tissue and Organ Culture,* 38:1, 77-79 (1994); Curtis, et al., *Journal of Experimental Botany,* 45:279, 1441-1449 (1994); Nagata, et al., *Journal for the American Society for Horticultural Science,* 125:6, 669-672 (2000); and Ibrahim, et al., *Plant Cell Tissue and Organ Culture,* 28(2), 139-145 (1992). It is clear from the literature that the state of the art is such that these methods of obtaining plants are routinely used and have a very high rate of success. Thus, another aspect of this invention is to provide cells which upon growth and differentiation produce lettuce plants having the physiological and morphological characteristics of variety 'Ezthana' or 'Eztron'.

As used herein, the term "tissue culture" indicates a composition containing isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture containing organs has been used to produce regenerated plants. U.S. Pat. Nos. 5,959,185, 5,973,234, and 5,977,445 describe certain techniques, the disclosures of which are incorporated herein by reference.

Additional Breeding Methods

The invention is also directed to methods for producing a lettuce plant by crossing a first parent lettuce plant with a second parent lettuce plant where the first or second parent lettuce plant is a lettuce plant of variety 'Ezthana' or 'Eztron'. Further, both first and second parent lettuce plants can come from lettuce variety 'Ezthana' or 'Eztron'. Thus, any such methods using lettuce variety 'Ezthana' or 'Eztron' are part of the invention: selfing, backcrosses, hybrid production, crosses to populations, and the like. All plants produced using lettuce variety 'Ezthana' or 'Eztron' as at least one parent are within the scope of this invention, including those developed from varieties derived from lettuce variety 'Ezthana' or 'Eztron'. Advantageously, this lettuce variety could be used in crosses with other, different, lettuce plants to produce the first generation ($F_1$) lettuce hybrid seeds and plants with superior characteristics. The variety of the invention can also be used for transformation where exogenous genes are introduced and expressed by the variety of the invention. Genetic variants created either through traditional breeding methods using lettuce variety 'Ezthana' or 'Eztron', or through transformation of variety 'Ezthana' or 'Eztron' by any of a number of protocols known to those of skill in the art are intended to be within the scope of this invention.

The following describes breeding methods that may be used with lettuce variety 'Ezthana' or 'Eztron' in the development of further lettuce plants. One such embodiment is a method for developing variety 'Ezthana' or 'Eztron' progeny lettuce plants in a lettuce plant breeding program, by: obtaining the lettuce plant, or a part thereof, of variety 'Ezthana' or 'Eztron', utilizing said plant or plant part as a source of breeding material, and selecting a lettuce variety 'Ezthana' or 'Eztron' progeny plant with molecular markers in common with variety 'Ezthana' or 'Eztron' and/or with morphological and/or physiological characteristics selected from the characteristics listed in the section entitled "Objective description of the variety 'Ezthana'" or "Objective description of the variety 'Eztron'". Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of lettuce variety 'Ezthana' or 'Eztron' progeny lettuce plants, by crossing variety 'Ezthana' or 'Eztron' with another lettuce plant, thereby producing a population of lettuce plants, which, on average, derive 50% of their alleles from lettuce variety 'Ezthana' or 'Eztron'. A plant of this population may be selected and repeatedly selfed or sibbed with a lettuce variety resulting from these successive filial generations. One embodiment of this invention is the lettuce variety produced by this method and that has obtained at least 50% of its alleles from lettuce variety 'Ezthana' or 'Eztron'. One of ordinary skill in the art of plant breeding would know how to evaluate the traits of two plant varieties to determine if there is no significant difference between the two traits expressed by those varieties. For example, see Fehr and Walt, *Principles of Variety Development*, pp. 261-286 (1987). Thus, the invention includes lettuce variety 'Ezthana' or 'Eztron' progeny lettuce plants containing a combination of at least two variety 'Ezthana' or 'Eztron' traits selected from those listed in the section entitled "Objective description of the variety 'Ezthana'" or "Objective description of the variety 'Eztron'", or the variety 'Ezthana' or 'Eztron' combination of traits listed in the Summary of the Invention, so that said progeny lettuce plant is not significantly different for said traits than lettuce variety 'Ezthana' or 'Eztron' as determined at the 5% significance level when grown in the same environmental conditions. Using techniques described herein, molecular markers may be used to identify said progeny plant as a lettuce variety 'Ezthana' or 'Eztron' progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of lettuce variety 'Ezthana' or 'Eztron' may also be characterized through their filial relationship with lettuce variety 'Ezthana' or 'Eztron', as for example, being within a certain number of breeding crosses of lettuce variety 'Ezthana' or 'Eztron'. A breeding cross is a cross made to introduce new genetics into the progeny, and is distinguished from a cross, such as a self or a sib cross, made to select among existing genetic alleles. The lower the number of breeding crosses in the pedigree, the closer the relationship between lettuce variety 'Ezthana' or 'Eztron' and its progeny. For example, progeny produced by the methods described herein may be within 1, 2, 3, 4, or 5 breeding crosses of lettuce variety 'Ezthana' or 'Eztron'.

As used herein, the term "plant" includes plant cells, plant protoplasts, plant cell tissue cultures from which lettuce plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

Lettuce Variety 'Ezthana'

A deposit of the lettuce variety 'Ezthana' is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of lettuce variety 'Ezthana' were deposited on Aug. 3, 2018 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 43135. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed for the enforceable life of the patent.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Lettuce Variety 'Eztron'

A deposit of the lettuce variety 'Eztron' is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of lettuce variety 'Eztron' were deposited on Aug. 3, 2018 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 43136. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed for the enforceable life of the patent.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. A lettuce seed selected from the group consisting of a lettuce seed designated as 'Ezthana', representative sample of seed having been deposited under NCIMB Accession Number 43135; and a lettuce seed designated as 'Eztron', representative sample of seed having been deposited under NCIMB Accession Number 43136.

2. A lettuce plant produced by growing the seed of claim 1.

3. A plant part from the plant of claim 2.

4. The plant part of claim 3, wherein said part is a head, a leaf, or a portion thereof.

5. The plant part of claim 4, wherein said part is a head.

6. A lettuce plant having all the physiological and morphological characteristics of the lettuce plant of claim 2.

7. A plant part from the plant of claim 6.

8. The plant part of claim 7, wherein said part is a head, a leaf, or a portion thereof.

9. The plant part of claim 8, wherein said part is a head.

10. An $F_1$ hybrid lettuce plant having 'Ezthana' as a parent where 'Ezthana' is grown from the seed of claim 1.

11. An $F_1$ hybrid lettuce plant having 'Eztron' as a parent where 'Eztron' is grown from the seed of claim 1.

12. A pollen grain or an ovule of the plant of claim 2.

13. A tissue culture of the plant of claim 2.

14. A lettuce plant regenerated from the tissue culture of claim 13, wherein the plant has all of the morphological and physiological characteristics of a lettuce plant produced by growing seed designated as 'Ezthana', representative sample of seed having been deposited under NCIMB Accession Number 43135.

15. A lettuce plant regenerated from the tissue culture of claim 13, wherein the plant has all of the morphological and physiological characteristics of a lettuce plant produced by growing seed designated as 'Eztron', representative sample of seed having been deposited under NCIMB Accession Number 43136.

16. A method of making lettuce seeds, said method comprising crossing the plant of claim 2 with another lettuce plant and harvesting seed therefrom.

17. A method of making lettuce variety 'Ezthana', said method comprising selecting seeds from the cross of one 'Ezthana' plant with another 'Ezthana' plant, a sample of 'Ezthana' lettuce seed having been deposited under NCIMB Accession Number 43135.

18. A method of making lettuce variety 'Eztron', said method comprising selecting seeds from the cross of one 'Eztron' plant with another 'Eztron' plant, a sample of 'Eztron' lettuce seed having been deposited under NCIMB Accession Number 43136.

* * * * *